(12) United States Patent
Kurnik

(10) Patent No.: US 6,272,364 B1
(45) Date of Patent: Aug. 7, 2001

(54) METHOD AND DEVICE FOR PREDICTING PHYSIOLOGICAL VALUES

(75) Inventor: Ronald T. Kurnik, Foster City, CA (US)

(73) Assignee: Cygnus, Inc., Redwood City, CA (US)

(*) Notice: Subject to any disclaimer, the term of this patent is extended or adjusted under 35 U.S.C. 154(b) by 0 days.

(21) Appl. No.: 09/309,720

(22) Filed: May 11, 1999

Related U.S. Application Data

(60) Provisional application No. 60/085,341, filed on May 13, 1998.

(51) Int. Cl.$^7$ .................................................. A61B 5/05
(52) U.S. Cl. ..................... 600/345; 600/365; 600/372; 600/396; 600/573
(58) Field of Search .................................. 600/300, 309, 600/310, 322, 345, 347, 365, 573, 575, 549, 395–396, 372, 393, 386; 607/115, 148–149

(56) References Cited

U.S. PATENT DOCUMENTS

| | | |
|---|---|---|
| 4,819,752 | 4/1989 | Zelin . |
| 4,970,145 | 11/1990 | Bennetto et al. . |
| 5,036,861 | 8/1991 | Sembrowich et al. . |
| 5,076,273 | 12/1991 | Schoendorfer et al. . |
| 5,086,229 | 2/1992 | Rosenthal et al. . |
| 5,139,023 | 8/1992 | Stanley et al. . |
| 5,140,985 | 8/1992 | Schroeder et al. . |
| 5,267,152 | 11/1993 | Yang et al. . |
| 5,279,543 | 1/1994 | Glikfeld et al. . |
| 5,362,307 | 11/1994 | Guy et al. . |
| 5,730,714 | 3/1998 | Guy et al. . |
| 5,735,273 | 4/1998 | Kurnik et al. . |
| 5,771,890 | 6/1998 | Tamada . |
| 5,822,715 | * 10/1998 | Worthington et al. ........... 600/309 X |
| 5,827,183 | 10/1998 | Kurnik et al. . |

FOREIGN PATENT DOCUMENTS

| | | |
|---|---|---|
| 42 21 848 A1 | 1/1994 | (DE) . |
| 4221848 | 1/1994 | (DE) . |
| WO 95/02357 | 1/1995 | (WO) . |
| WO 96/00109 | 1/1996 | (WO) . |
| WO 96/00110 | 1/1996 | (WO) . |
| WO 97/24059 | 7/1997 | (WO) . |

OTHER PUBLICATIONS

Bremer et al., "Perspectives in Diabetes—Is Blood Glucose Predictable From Previous Values?—A Solicitation for Data," *Diabetes* 48:445–451 (1999).

Diggle, "Times Series: A Biostatistical Introduction," Chapters 2–4, 6 and 7, Oxford University Press, Oxford (1990).

Kurnik et al., "Application of Neural Networks to Optimize Flux Profiles for Transdermal Systems," Chapter 15 in *Intelligent Materials for Controlled Released*, (Dinh et al., eds) pp. 205–218 (1999).

The Diabetes Control and Complications Trial Research, *New Engl. J. Med.* 329:977–1036 (1993).

* cited by examiner

*Primary Examiner*—John P. Lacyk
*Assistant Examiner*—Ryan Carter
(74) *Attorney, Agent, or Firm*—Barbara G. McClung; Robins & Associates

(57) ABSTRACT

A method and device are provided for measuring the concentration of target chemical analytes present in a biological system, and then predicting a future or past concentration of an analyte using a series of such measurements. One important application of the invention involves predicting future or past blood glucose concentrations using a series of measured blood glucose values.

46 Claims, 7 Drawing Sheets

METHOD AND DEVICE FOR PREDICTING PHYSIOLOGICAL VALUES

CROSS-REFERENCE TO RELATED APPLICATION

This application is related to provisional patent application Ser. No. 60/085,341, filed May 13, 1998, from which priority is claimed under 35 USC §119(e)(1) and which application is incorporated herein by reference in its entirety.

FIELD OF THE INVENTION

The invention relates generally to a method and device for measuring the concentration of target chemical analytes present in a biological system. More particularly, the invention relates to a method and device for predicting a future or past concentration of an analyte using a series of measurements obtained from a monitoring system. One important application of the invention involves predicting future or past blood glucose concentrations.

BACKGROUND OF THE INVENTION

The generally accepted methods for time series forecasting are: extrapolation of linear regression, extrapolation of polynomial regression, autoregressive moving average (ARMA), and exponential smoothing as discussed by Diggle, *Time Series: A Biostatistical Introduction*, Oxford University Press, Oxford, (1990). Linear regression models are an acceptable means of forecasting, provided that the data being analyzed are linear. In the case where the data in question are nonlinear, polynomial regression is often used to model the data.

Autoregressive (ARMA) methods have been used with success in forecasting where the underlying phenomena are stationary (or can be converted to stationary), with superimposed fluctuations expressible as random white noise. These two requirements can be met for some physiologic variables, but plasma glucose levels in diabetic patients generally do not fit these requirements. The method of exponential smoothing is a special case of the ARMA method. The above methods forecast the future value of a variable based on the value of that variable at previous time points. Information on the first and second derivative of the variable with respect to time is not included. Inclusion of these time derivatives can substantially increase the accuracy of the forecasting method in the situation where the future value of a variable depends on its time rate of change.

SUMMARY OF THE INVENTION

The present invention provides a method and device for continually or continuously measuring the concentration of an analyte present in a biological system. The method entails continually or continuously detecting a raw signal from the biological system, wherein the raw signal is specifically related to the analyte. As the raw signals are obtained, a calibration step is performed to correlate raw signal with a measurement value indicative of the concentration of analyte present in the biological system. These steps of detection and calibration are used to obtain a series of measurement values at selected time intervals. In a preferred embodiment, the selected time intervals are evenly spaced. Once the series of measurement values is obtained, the method of the invention provides for the prediction of a measurement value at a further time interval which occurs either one time interval before, or one time interval after, the series of measurement values is obtained.

The raw signal can be obtained using any suitable sensing methodology including, for example, methods which rely on direct contact of a sensing apparatus with the biological system; methods which extract samples from the biological system by invasive, minimally invasive, and non-invasive sampling techniques, wherein the sensing apparatus is contacted with the extracted sample; methods which rely on indirect contact of a sensing apparatus with the biological system; and the like. In preferred embodiments of the invention, methods are used to extract samples from the biological sample using minimally invasive or non-invasive sampling techniques. The sensing apparatus used with any of the above-noted methods can employ any suitable sensing element to provide the raw signal including, but not limited to, physical, chemical, electrochemical, photochemical, spectrophotometric, polarimetric, calorimetric, radiometric, or like elements. In preferred embodiments of the invention, a biosensor is used which comprises an electrochemical sensing element.

In one particular embodiment of the invention, the raw signal is obtained using a transdermal sampling system that is placed in operative contact with a skin or mucosal surface of the biological system. The sampling system transdermally extracts the analyte from the biological system using any appropriate sampling technique, for example, iontophoresis. The transdermal sampling system is maintained in operative contact with the skin or mucosal surface of the biological system to provide for such continual or continuous analyte measurement.

The analyte can be any specific substance or component that one is desirous of detecting and/or measuring in a chemical, physical, enzymatic, or optical analysis. Such analytes include, but are not limited to, amino acids, enzyme substrates or products indicating a disease state or condition, other markers of disease states or conditions, drugs of abuse, therapeutic and/or pharmacologic agents, electrolytes, physiological analytes of interest (e.g., calcium, potassium, sodium, chloride, bicarbonate ($CO_2$), glucose, urea (blood urea nitrogen), lactate, hematocrit, and hemoglobin), lipids, and the like. In preferred embodiments, the analyte is a physiological analyte of interest, for example glucose, or a chemical that has a physiological action, for example a drug or pharmacological agent.

A wide variety of mathematical techniques can be used to predict the measurement value at the further time interval (e.g., to predict unmeasured values at future or past time intervals). However, in a preferred embodiment of the invention, a Taylor Series Exponential Smoothing (TSES) function is used to predict measurement values. The TSES function is represented by the following equation:

$$y_{n+1} = y_n + \alpha(y_n - y_{n-1}) + \frac{\alpha^2}{2}(y_n - 2y_{n-1} + y_{n-2})$$

wherein: $\alpha$ is an optimizable variable which is a real number of between 0 and 1 and is adjusted based on the particular measurements obtained and the relationship between those measurements and actual results; n is a time interval; and y is an analyte concentration or signal converted to an analyte concentration which signal measurement is optimized to fit the results sought e.g., to correspond with a reference analyte concentration.

Accordingly, it is an object of the invention to obtain a series of measurement values taken at selected time intervals, and then use the TSES function of the invention to predict a future measurement value occurring one time interval after the series is taken. In one particular aspect of the invention, the predicted future value is used to eliminate or substantially reduce a lag time inherent in a transdermal extraction sampling system.

It is also an object of the invention to obtain a series of measurement values taken at evenly spaced time intervals, and then use the TSES function of the invention to predict a past measurement value occurring one time interval prior to the time when the series is taken. In one particular aspect of the invention, the predicted past value is used in a calibration step to calibrate a sampling device.

It is a still further object of the invention to use the TSES function of the invention to predict future or past blood glucose values. In one aspect, the method of the invention is used in conjunction with an iontophoretic sampling device that provides continual or continuous blood glucose measurements. In another aspect of the invention, a predicted future value obtained using the subject TSES function is used to control an aspect of the biological system, particularly a physiological effect.

It is yet a further object of the invention to provide a method for measuring blood glucose in a subject. The method entails operatively contacting a glucose sensing apparatus with the subject to detect blood glucose and thus obtain a raw signal from the sensing apparatus. The raw signal is specifically related to the glucose, and is converted into a measurement value indicative of the subject's blood glucose concentration using a calibration step. Further raw signals are obtained and converted into measurement values in order to obtain a series of measurement values at selected time intervals, and the series of measurements is then used to predict a glucose measurement value at a further time interval. In one aspect of the invention, the sensing apparatus is a near-IR spectrometer.

It is also an object of the invention to provide a monitoring system for continually or continuously measuring an analyte present in a biological system. The monitoring system is formed from the operative combination of a sampling means, a sensing means, and a microprocessor means which controls the sampling means and the sensing means. The sampling means is used to continually or continuously extract the analyte from the biological system across a skin or mucosal surface of said biological system. The sensing means is arranged in operative contact with the analyte extracted by the sampling means, such that the sensing means can obtain a raw signal from the extracted analyte which signal is specifically related to the analyte. The microprocessor means communicates with the sampling means and the sensing means, and is used to: (a) control the sampling means and the sensing means to obtain a series of raw signals at selected time intervals during a continual or continuous measurement period; (b) correlate the raw signals with measurement values indicative of the concentration of analyte present in the biological system; and (c) predict a measurement value at a further time interval which occurs either one time interval before or one time interval after the series of measurement values is obtained. In one aspect, the monitoring system uses an iontophoretic current to extract the analyte from the biological system.

It is a further object of the invention to provide a monitoring system for measuring blood glucose in a subject. The monitoring system is formed from an operative combination of a sensing means and a microprocessor means. The sensing means is adapted for operative contact with the subject or with a glucose-containing sample extracted from the subject, and is used to obtain a raw signal specifically related to blood glucose in the subject. The microprocessor means communicates with the sensing means, and is used to: (a) control the sensing means to obtain a series of raw signals (specifically related to blood glucose) at selected time intervals; (b) correlate the raw signals with measurement values indicative of the concentration of blood glucose present in the subject; and (c) predict a measurement value at a further time interval which occurs either one time interval before or one time interval after the series of measurement values is obtained. In one aspect, the monitoring system comprises a biosensor having an electrochemical sensing element. In another aspect, the monitoring system comprises a near-IR spectrometer.

In a further aspect, the methods and devices of the present invention can include enhancement of skin permeability by pricking the skin with micro-needles when the biological system includes skin, or, for example, a mucosal surface. Such pricking with micro-needles can facilitate extraction an analyte of interest from the biological system.

Additional objects, advantages and novel features of the invention will be set forth in part in the description which follows, and in part will become apparent to those skilled in the art upon examination of the following, or may be learned by practice of the invention.

DETAILED DESCRIPTION OF THE PREFERRED EMBODIMENTS

Figure 1A:
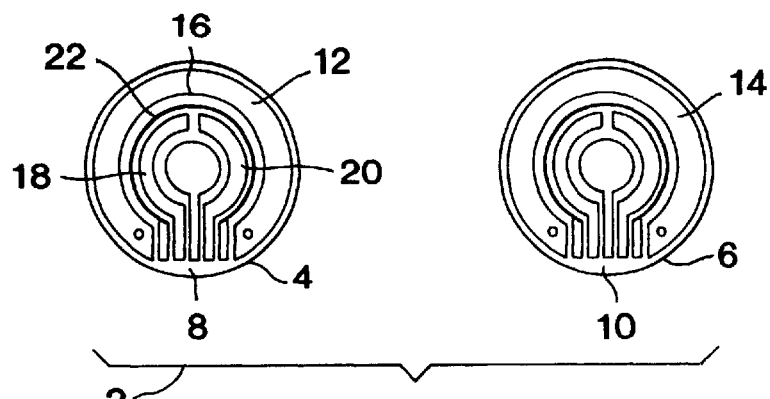
FIG. 1A depicts a top plan view of an iontophoretic collection reservoir and electrode assembly for use in a transdermal sampling device constructed according to the present invention.

Before describing the present invention in detail, it is to be understood that this invention is not limited to particular compositions or biological systems as such may, of course, vary. It is also to be understood that the terminology used herein is for the purpose of describing particular embodiments only, and is not intended to be limiting.

As used in this specification and the appended claims, the singular forms "a", "an" and "the" include plural referents unless the content clearly dictates otherwise. Thus, for example, reference to "an analyte" includes mixtures of analytes, and the like.

All publications, patents and patent applications cited herein, whether supra or infra, are hereby incorporated by reference in their entirety.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

In describing and claiming the present invention, the following terminology will be used in accordance with the definitions set out below.

Definitions

The terms "analyte" and "target analyte" are used herein to denote any physiological analyte of interest that is a specific substance or component that is being detected and/or measured in a chemical, physical, enzymatic, or optical analysis. A detectable signal (e.g., a chemical signal or electrochemical signal) can be obtained, either directly or indirectly, from such an analyte or derivatives thereof. Furthermore, the terms "analyte" and "substance" are used interchangeably herein, and are intended to have the same meaning, and thus encompass any substance of interest. In preferred embodiments, the analyte is a physiological analyte of interest, for example, glucose, or a chemical that has a physiological action, for example, a drug or pharmacological agent.

A "sampling device" or "sampling system" refers to any device for obtaining a sample from a biological system for the purpose of determining the concentration of an analyte of interest. As used herein, the term "sampling" means invasive, minimally invasive or non-invasive extraction of a substance from the biological system, generally across a membrane such as skin or mucosa. The membrane can be natural or artificial, and can be of plant or animal nature, such as natural or artificial skin, blood vessel tissue, intestinal tissue, and the like. Typically, the sampling means are in operative contact with a "reservoir," or "collection reservoir," wherein the sampling means is used for extracting the analyte from the biological system into the reservoir to obtain the analyte in the reservoir. A "biological system" includes both living and artificially maintained systems. Examples of minimally invasive and noninvasive sampling techniques include iontophoresis, sonophoresis, suction, electroporation, thermal poration, passive diffusion, microfine (miniature) lances or cannulas, subcutaneous implants or insertions, and laser devices. Sonophoresis uses ultrasound to increase the permeability of the skin (see, e.g., Menon et al. (1994) *Skin Pharmacology* 7:130–139). Suitable sonophoresis sampling systems are described in International Publication No. WO 91/12772, published Sep. 5, 1991. Passive diffusion sampling devices are described, for example, in International Publication Nos.: WO 97/38126 (published Oct. 16, 1997); WO 97/42888, WO 97/42886, WO 97/42885, and WO 97/42882 (all published Nov. 20, 1997); and WO 97/43962 (published Nov. 27, 1997). Laser devices use a small laser beam to burn a hole through the upper layer of the patient's skin (see, e.g., Jacques et al. (1978) *J. Invest. Dermatology* 88:88–93). Examples of invasive sampling techniques include traditional needle and syringe or vacuum sample tube devices.

The term "collection reservoir" is used to describe any suitable containment means for containing a sample extracted from a biological system. For example, the collection reservoir can be a receptacle containing a material which is ionically conductive (e.g., water with ions therein), or alternatively, it can be a material, such as, a sponge-like material or hydrophilic polymer, used to keep the water in place. Such collection reservoirs can be in the form of a hydrogel (for example, in the form of a disk or pad). Hydrogels are typically referred to as "collection inserts." Other suitable collection reservoirs include, but are not limited to, tubes, vials, capillary collection devices, cannulas, and miniaturized etched, ablated or molded flow paths.

A "housing" for the sampling system can further include suitable electronics (e.g., microprocessor, memory, display and other circuit components) and power sources for operating the sampling system in an automatic fashion.

A "monitoring system," as used herein, refers to a system useful for continually or continuously measuring a physiological analyte present in a biological system. Such a system typically includes, but is not limited to, sampling means, sensing means, and a microprocessor means in operative communication with the sampling means and the sensing means.

The term "artificial," as used herein, refers to an aggregation of cells of monolayer thickness or greater which are grown or cultured in vivo or in vitro, and which function as a tissue of an organism but are not actually derived, or excised, from a pre-existing source or host.

The term "subject" encompasses any warm-blooded animal, particularly including a member of the class Mammalia such as, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

As used herein, the term "continual measurement" intends a series of two or more measurements obtained from a particular biological system, which measurements are obtained using a single device maintained in operative contact with the biological system over the time period in which the series of measurements is obtained. The term thus includes continuous measurements.

The term "transdermal," as used herein, includes both transdermal and transmucosal techniques, i.e., extraction of a target analyte across skin or mucosal tissue. Aspects of the invention which are described herein in the context of "transdermal," unless otherwise specified, are meant to apply to both transdermal and transmucosal techniques.

The term "transdermal extraction," or "transdermally extracted" intends any noninvasive, or at least minimally invasive sampling method, which entails extracting and/or transporting an analyte from beneath a tissue surface across skin or mucosal tissue. The term thus includes extraction of an analyte using iontophoresis (reverse iontophoresis), electroosmosis, sonophoresis, microdialysis, suction, and passive diffusion. These methods can, of course, be coupled with application of skin penetration enhancers or skin permeability enhancing technique such as tape stripping or pricking with micro-needles. The term "transdermally extracted" also encompasses extraction techniques which employ thermal poration, electroporation, microfine lances, microfine canulas, subcutaneous implants or insertions, and the like.

The term "iontophoresis" intends a method for transporting substances across tissue by way of an application of electrical energy to the tissue. In conventional iontophoresis, a reservoir is provided at the tissue surface to serve as a container of material to be transported. Iontophoresis can be carried out using standard methods known to those of skill in the art, for example, by establishing an electrical potential using a direct current (DC) between fixed anode and cathode "iontophoretic electrodes," alternating a direct current between anode and cathode iontophoretic electrodes, or using a more complex waveform such as applying a current with alternating polarity (AP) between iontophoretic electrodes (so that each electrode is alternately an anode or a cathode).

The term "reverse iontophoresis" refers to the movement of a substance from a biological fluid across a membrane by way of an applied electric potential or current. In reverse iontophoresis, a reservoir is provided at the tissue surface to receive the extracted material.

"Electroosmosis" refers to the movement of a substance through a membrane by way of an electric field-induced convective flow. The terms iontophoresis, reverse iontophoresis, and electroosmosis, will be used interchangeably herein to refer to movement of any ionically charged or uncharged substance across a membrane (e.g., an epithelial membrane) upon application of an electric potential to the membrane through an ionically conductive medium.

The term "sensing device," "sensing means," or "biosensor device" encompasses any device that can be used to measure the concentration of an analyte, or derivative thereof, of interest. Preferred sensing devices for detecting blood analytes generally include electrochemical devices and chemical devices. Examples of electrochemical devices include the Clark electrode system (see, e.g., Updike, et al., (1967) *Nature* 214:986–988), and other amperometric, coulometric, or potentiometric electrochemical devices. Examples of chemical devices include conventional enzyme-based reactions as used in the Lifescan® glucose monitor (Johnson and Johnson, New Brunswick, N.J.) (see, e.g., U.S. Pat. No. 4,935,346 to Phillips, et al.).

A "biosensor" or "biosensor device" includes, but is not limited to, a "sensor element" which includes, but is not limited to, a "biosensor electrode" or "sensing electrode" or "working electrode" which refers to the electrode that is monitored to determine the amount of electrical signal at a point in time or over a given time period, which signal is then correlated with the concentration of a chemical compound. The sensing electrode comprises a reactive surface which converts the analyte, or a derivative thereof, to electrical signal. The reactive surface can be comprised of any electrically conductive material such as, but not limited to, platinum-group metals (including, platinum, palladium, rhodium, ruthenium, osmium, and iridium), nickel, copper, silver, and carbon, as well as, oxides, dioxides, combinations or alloys thereof. Some catalytic materials, membranes, and fabrication technologies suitable for the construction of amperometric biosensors were described by Newman, J. D., et al. (*Analytical Chemistry* 67(24), 4594–4599, 1995).

The "sensor element" can include components in addition to a biosensor electrode, for example, it can include a "reference electrode," and a "counter electrode." The term "reference electrode" is used herein to mean an electrode that provides a reference potential, e.g., a potential can be established between a reference electrode and a working electrode. The term "counter electrode" is used herein to mean an electrode in an electrochemical circuit which acts as a current source or sink to complete the electrochemical circuit. Although it is not essential that a counter electrode be employed where a reference electrode is included in the circuit and the electrode is capable of performing the function of a counter electrode, it is preferred to have separate counter and reference electrodes because the reference potential provided by the reference electrode is most stable when it is at equilibrium. If the reference electrode is required to act further as a counter electrode, the current flowing through the reference electrode may disturb this equilibrium. Consequently, separate electrodes functioning as counter and reference electrodes are most preferred.

In one embodiment, the "counter electrode" of the "sensor element" comprises a "bimodal electrode." The term "bimodal electrode" as used herein typically refers to an electrode which is capable of functioning non-simultaneously as, for example, both the counter electrode (of the "sensor element") and the iontophoretic electrode (of the "sampling means").

The terms "reactive surface," and "reactive face" are used interchangeably herein to mean the surface of the sensing electrode that: (1) is in contact with the surface of an electrolyte containing material (e.g. gel) which contains an analyte or through which an analyte, or a derivative thereof, flows from a source thereof; (2) is comprised of a catalytic material (e.g., carbon, platinum, palladium, rhodium, ruthenium, or nickel and/or oxides, dioxides and combinations or alloys thereof) or a material that provides sites for electrochemical reaction; (3) converts a chemical signal (e.g. hydrogen peroxide) into an electrical signal (e.g., an electrical current); and (4) defines the electrode surface area that, when composed of a reactive material, is sufficient to drive the electrochemical reaction at a rate sufficient to generate a detectable, reproducibly measurable, electrical signal that is correlatable with the amount of analyte present in the electrolyte.

The term "collection reservoir" and "collection insert" are used to describe any suitable containment means for containing a sample extracted from a biological system. The reservoir can include a material which is ionically conductive (e.g., water with ions therein), wherein another material such as a sponge-like material or hydrophilic polymer is used to keep the water in place. Such collection reservoirs can be in the form of a hydrogel (for example, in the shape of a disk or pad). Other suitable collection reservoirs include, but are not limited to, tubes, vials, capillary collection devices, cannulas, and miniaturized etched, ablated or molded flow paths.

An "ionically conductive material" refers to any material that provides ionic conductivity, and through which electrochemically active species can diffuse. The ionically conductive material can be, for example, a solid, liquid, or semi-solid (e.g., in the form of a gel) material that contains an electrolyte, which can be composed primarily of water and ions (e.g., sodium chloride), and generally comprises 50% or more water by weight. The material can be in the form of a gel, a sponge or pad (e.g., soaked with an electrolytic solution), or any other material that can contain an electrolyte and allow passage therethrough of electrochemically active species, especially the analyte of interest.

The term "physiological effect" encompasses effects produced in the subject that achieve the intended purpose of a therapy. In preferred embodiments, a physiological effect means that the symptoms of the subject being treated are prevented or alleviated. For example, a physiological effect would be one that results in the prolongation of survival in a patient.

A "laminate", as used herein, refers to structures comprised of at least two bonded layers. The layers may be bonded by welding or through the use of adhesives. Examples of welding include, but are not limited to, the following: ultrasonic welding, heat bonding, and inductively coupled localized heating followed by localized flow. Examples of common adhesives include, but are not limited to, pressure sensitive adhesives, thermoset adhesives, cyanocrylate adhesives, epoxies, contact adhesives, and heat sensitive adhesives.

A "collection assembly", as used herein, refers to structures comprised of several layers, where the assembly includes at least one collection insert, for example a hydrogel. An example of a collection assembly of the present invention is a mask layer, collection inserts, and a retaining layer where the layers are held in appropriate, functional relationship to each other but are not necessarily a laminate, i.e., the layers may not be bonded together. The layers may, for example, be held together by interlocking geometry or friction.

An "autosensor assembly", as used herein, refers to structures generally comprising a mask layer, collection inserts, a retaining layer, an electrode assembly, and a support tray. The autosensor assembly may also include liners. The layers of the assembly are held in appropriate, functional relationship to each other.

The mask and retaining layers are preferably composed of materials that are substantially impermeable to the analyte (chemical signal) to be detected (e.g., glucose); however, the material can be permeable to other substances. By "substantially impermeable" is meant that the material reduces or eliminates chemical signal transport (e.g., by diffusion). The material can allow for a low level of chemical signal transport, with the proviso that chemical signal that passes through the material does not cause significant edge effects at the sensing electrode.

"Substantially planar" as used herein, includes a planar surface that contacts a slightly curved surface, for example, a forearm or upper arm of a subject. A "substantially planar" surface is, for example, a surface having a shape to which skin can conform, i.e., contacting contact between the skin and the surface.

By the term "printed" as used herein is meant a substantially uniform deposition of an electrode formulation onto one surface of a substrate (i.e., the base support). It will be appreciated by those skilled in the art that a variety of techniques may be used to effect substantially uniform deposition of a material onto a substrate, e.g., Gravure-type printing, extrusion coating, screen coating, spraying, painting, or the like.

The term "Taylor Series Exponential Smoothing Function ("TSES")" encompasses mathematical functions (algorithms) for predicting the behavior of a variable at a different point in time, which factors in the slope, and the rate of change of the slope. An example of a TSES function useful in connection with the present invention is a TSES function represented by:

$$y_{n+1} = y_n + \alpha(y_n - y_{n-1}) + \frac{\alpha^2}{2}(y_n - 2y_{n-1} + y_{n-2})$$

wherein: $\alpha$ is an optimizable variable which is a real number of between 0 and 1, and is adjusted based on the particular measurements obtained and the relationship between those measurements and actual results; n is an evenly spaced time interval; and y is an analyte concentration or signal converted to an analyte concentration which signal measurement is optimized to fit the results sought, e.g., to correspond with a reference analyte concentration.

A "future time point" refers to the time point in the future at which the concentration of the analyte of interest is predicted. In preferred embodiments, this term refers to a time point that is one time interval ahead, where a time interval is the amount of time between sampling and sensing events.

General Methods

The present invention relates to use of a sensing device for measuring the concentration of a target analyte present in a biological system. In preferred embodiments, the sensing device comprises a biosensor. In other preferred embodiments, a sampling device is used to extract small amounts of a target analyte from the biological system, and then sense and/or quantify the concentration of the target analyte. Measurement with the biosensor and/or sampling with the sampling device can be carried out in a continual manner. Continual measurement allows for closer monitoring of target analyte concentration fluctuations.

The analyte can be any specific substance or component that one is desirous of detecting and/or measuring in a chemical, physical, enzymatic, or optical analysis. Such analytes include, but are not limited to, amino acids, enzyme substrates or products indicating a disease state or condition, other markers of disease states or conditions, drugs of abuse, therapeutic and/or pharmacologic agents (e.g., theophylline, anti-HIV drugs, lithium, anti-epileptic drugs, cyclosporin, chemotherapeutics), electrolytes, physiological analytes of interest (e.g., urate/uric acid, carbonate, calcium, potassium, sodium, chloride, bicarbonate ($CO_2$), glucose, urea (blood urea nitrogen) lactate/lactic acid, hydroxybutyrate, cholesterol, triglycerides, creatine, creatinine, insulin, hematocrit, and hemoglobin), blood gases (carbon dioxide, oxygen, pH), lipids, heavy metals (e.g., lead, copper), and the like. In preferred embodiments, the analyte is a physiological analyte of interest, for example glucose, or a chemical that has a physiological action, for example a drug or pharmacological agent.

In order to facilitate detection of the analyte, an enzyme can be disposed in the collection reservoir, or, if several collection reservoirs are used, the enzyme can be disposed in several or all of the reservoirs. The selected enzyme is capable of catalyzing a reaction with the extracted analyte (in this case glucose) to the extent that a product of this reaction can be sensed, e.g., can be detected electrochemically from the generation of a current which current is detectable and proportional to the concentration or amount of the analyte which is reacted. A suitable enzyme is glucose oxidase which oxidizes glucose to gluconic acid and hydrogen peroxide. The subsequent detection of hydrogen peroxide on an appropriate biosensor electrode generates two electrons per hydrogen peroxide molecule which create a current which can be detected and related to the amount of glucose entering the device. Glucose oxidase (GOx) is readily available commercially and has well known catalytic characteristics. However, other enzymes can also be used, so long as they specifically catalyze a reaction with an analyte or substance of interest to generate a detectable product in proportion to the amount of analyte so reacted.

In like manner, a number of other analyte-specific enzyme systems can be used in the invention, which enzyme systems operate on much the same general techniques. For example, a biosensor electrode that detects hydrogen peroxide can be used to detect ethanol using an alcohol oxidase enzyme system, or similarly uric acid with urate oxidase system, urea with a urease system, cholesterol with a cholesterol oxidase system, and theophylline with a xanthine oxidase system.

In addition, the oxidase enzyme (used for hydrogen peroxidase-based detection) can be replaced with another redox system, for example, the dehydrogenase-enzyme NAD-NADH, which offers a separate route to detecting additional analytes. Dehydrogenase-based sensors can use working electrodes made of gold or carbon (via mediated chemistry). Examples of analytes suitable for this type of monitoring include, but are not limited to, cholesterol, ethanol, hydroxybutyrate, phenylalanine, triglycerides, and urea. Further, the enzyme can be eliminated and detection can rely on direct electrochemical or potentiometric detection of an analyte. Such analytes include, without limitation, heavy metals (e.g., cobalt, iron, lead, nickel, zinc), oxygen, carbonate/carbon dioxide, chloride, fluoride, lithium, pH, potassium, sodium, and urea. Also, the sampling system described herein can be used for therapeutic drug monitoring, for example, monitoring anti-epileptic drugs (e.g., phenytion), chemotherapy (e.g., adriamycin), hyperactivity (e.g., ritalin), and anti-organ-rejection (e.g., cyclosporin).

In the general method of the invention, a raw signal is obtained from a sensing device, which signal is related to a target analyte present in the biological system. The raw signal can be obtained using any suitable sensing methodology including, for example, methods which rely on direct contact of a sensing apparatus with the biological system; methods which extract samples from the biological system by invasive, minimally invasive, and non-invasive sampling techniques, wherein the sensing apparatus is contacted with the extracted sample; methods which rely on indirect contact of a sensing apparatus with the biological system; and the like. In preferred embodiments of the invention, methods are used to extract samples from the biological sample using minimally invasive or non-invasive sampling techniques. The sensing apparatus used with any of the above-noted methods can employ any suitable sensing element to provide the signal including, but not limited to, physical, chemical, electrochemical, photochemical, spectrophotometric, polarimetric, calorimetric, radiometric, or like elements. In preferred embodiments of the invention, a biosensor is used which comprises an electrochemical sensing element.

In another embodiment of the invention, a near-IR glucose sensing apparatus is used to detect blood glucose in a subject, and thus generate the raw signal. A number of near-IR glucose sensing devices suitable for use in the present method are known in the art and are readily available. For example, a near-IR radiation diffuse-reflection laser spectroscopy device is described in U.S. Pat. No. 5,267,152 to Yang et al. Similar near-IR spectrometric devices are also described in U.S. Pat. No. 5,086,229 to Rosenthal et al. and U.S. Pat. No. 4,975,581 to Robinson et al. These near-IR devices use traditional methods of reflective or transmissive near infrared (near-IR) analysis to measure absorbance at one or more glucose-specific wavelengths, and can be contacted with the subject at an appropriate location, such as a finger-tip, skin fold, eyelid, or forearm surface to obtain the raw signal.

The raw signal obtained using any of the above-described methodologies is then converted into an analyte-specific value of known units to provide an interpretation of the signal obtained from the sensing device. The interpretation uses a mathematical transformation to model the relationship between a measured response in the sensing device and a corresponding analyte-specific value. Thus, a calibration step is used herein to relate, for example, an electrochemical signal (detected by a biosensor), or near-IR absorbance spectra (detected with a near-IR detector) with the concentration of a target analyte in a biological system.

Analyte-specific values are then used to predict future (time forecasting) or past (calibration) measurements of the target analyte concentration in the biological system. More particularly, a series of analyte-specific values are obtained, and this measurement series is then used to predict unmeasured analyte values at different points in time, e.g., future or past time points. In this manner, lag times inherent in certain sampling and/or sensing techniques can be eliminated to provide real-time measurement predictions.

The predicted analyte values can optionally be used in a subsequent step to control an aspect of the biological system. In one embodiment, predicted analyte values are used to determine when, and at what level, a constituent should be added to the biological system in order to control an aspect of the biological system. In a preferred embodiment, the analyte value can be used in a feedback control loop to control a physiological effect in the biological system.

The above general methods can, of course, be used with a wide variety of biological systems, target analytes, and/or sensing techniques. The determination of particularly suitable combinations is within the skill of the ordinarily skilled artisan when directed by the instant disclosure. Although these methods are broadly applicable to measuring any chemical analyte and/or substance in a biological system, the invention is expressly exemplified for use in a non-invasive, transdermal sampling system which uses an electrochemical biosensor to quantify or qualify glucose or a glucose metabolite.

Obtaining the Raw Signal.

The raw signal can be obtained using any sensing device that is operatively contacted with the biological system. Such sensing devices can employ physical, chemical, electrochemical, spectrophotometric, polarimetric, calorimetric, radiometric, or like measurement techniques. In addition, the sensing device can be in direct or indirect contact with the biological system, or used with a sampling device which extracts samples from the biological system using invasive, minimally invasive or non-invasive sampling techniques. In preferred embodiments, a minimally invasive or non-invasive sampling device is used to obtain samples from the biological system, and the sensing device comprises a biosensor with an electrochemical sensing element. In particularly preferred embodiments, a sampling device is used to obtain continual transdermal or transmucosal samples from a biological system, and the analyte of interest is glucose.

More specifically, a non-invasive glucose monitoring device is used to measure changes in glucose levels in an animal subject over a wide range of glucose concentrations. The sampling method is based on transdermal glucose extraction and the sensing method is based on electrochemical detection technology. The device can be contacted with the biological system continuously, and automatically obtains glucose samples in order to measure glucose concentration at preprogrammed intervals.

Sampling is carried out continually by non-invasively extracting glucose through the skin of the patient using an iontophoretic current. More particularly, an iontophoretic current is applied to a surface of the skin of a subject. When the current is applied, ions or charged molecules pull along other uncharged molecules or particles such as glucose which are drawn into a collection reservoir placed on the surface of the skin. The collection reservoir may comprise any ionically conductive material and is preferably in the form of a hydrogel which is comprised of a hydrophilic material, water and an electrolyte. The collection reservoir may further contain an enzyme which catalyzes a reaction between glucose and oxygen. The enzyme is preferably glucose oxidase (GOx) which catalyzes the reaction between glucose and oxygen and results in the production of hydrogen peroxide. The hydrogen peroxide reacts at a catalytic surface of a biosensor electrode, resulting in the generation of electrons which create a detectable biosensor current (raw signal). Based on the amount of biosensor current created over a given period of time, a measurement is taken, which measurement is related to the amount of glucose drawn into the collection reservoir over a given period of time. In a preferred embodiment the reaction is allowed to continue until substantially all of the glucose in the collection reservoir has been subjected to a reaction and is therefore no longer detectable, and the total biosensor current generated is related to the concentration of glucose in the subject.

When the reaction is complete, the process is repeated and a subsequent measurement is obtained. More specifically, the iontophoretic current is again applied, glucose is drawn through the skin surface into the collection reservoir, and the reaction is catalyzed in order to create a biosensor current. These sampling (extraction) and sensing operations are integrated such that glucose from interstitial fluid directly beneath the skin surface is extracted into the hydrogel collection pad where it contacts the GOx enzyme. The GOx enzyme converts glucose and oxygen in the hydrogel to hydrogen peroxide which diffuses to a Pt-based sensor and reacts with the sensor to regenerate oxygen and form electrons. The electrons generate an electrical signal that can be measured, analyzed, and correlated to blood glucose.

A generalized method for continual monitoring of a physiological analyte is disclosed in International Publication No. WO 97/24059, published Jul. 10, 1997, which publication is incorporated herein by reference. As noted in that publication, the analyte is extracted into a reservoir containing a hydrogel which is preferably comprised of a hydrophilic material of the type described in International Publication No. WO 97/02811, published Jan. 30, 1997, which publication is incorporated herein by reference. Suitable hydrogel materials include polyethylene oxide polyacrylic acid, polyvinylalcohol and related hydrophilic polymeric materials combined with water to form an aqueous gel.

In the above non-invasive glucose monitoring device, a biosensor electrode is positioned on a surface of the hydrogel opposite the surface contacting the skin. The sensor electrode acts as a detector which detects current generated by hydrogen peroxide in the redox reaction, or more specifically detects current which is generated by the electrons generated by the redox reaction catalyzed by the platinum surface of the electrode. The details of such electrode assemblies and devices for iontophoretic extraction of glucose are disclosed in International Publication No. WO 96/00110, published Jan. 4, 1996, and International Publication No. WO 97/10499, published Mar. 2, 1997, which publications are also incorporated herein by reference.

Figure 1B:
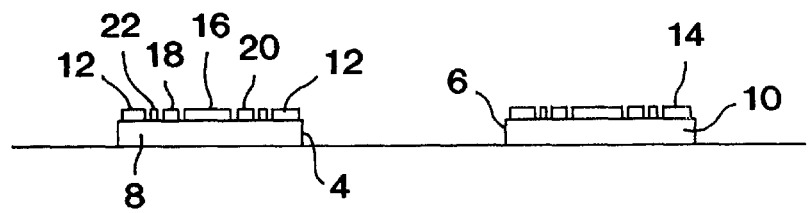
FIG. 1B depicts the side view of the iontophoretic collection reservoir and electrode assembly shown in FIG. 1A.

Referring now to FIGS. 1A and 1B, an iontophoretic collection reservoir and electrode assembly for use in a transdermal sensing device is generally indicated at 2. The assembly comprises two iontophoretic collection reservoirs, 4 and 6, each having a conductive medium 8, and 10 (preferably cylindrical hydrogel pads), respectively disposed therein. First (12) and second (14) ring-shaped iontophoretic electrodes are respectively contacted with conductive medium 8 and 10. The first iontophoretic electrode 12 surrounds three biosensor electrodes which are also contacted with the conductive medium 8, a working electrode 16, a reference electrode 18, and a counter electrode 20. A guard ring 22 separates the biosensor electrodes from the iontophoretic electrode 12 to minimize noise from the iontophoretic circuit. Conductive contacts provide communication between the electrodes and an associated power source and control means as described in detail below. A similar biosensor electrode arrangement can be contacted with the conductive medium 10, or the medium can not have a sensor means contacted therewith.

Figure 2:
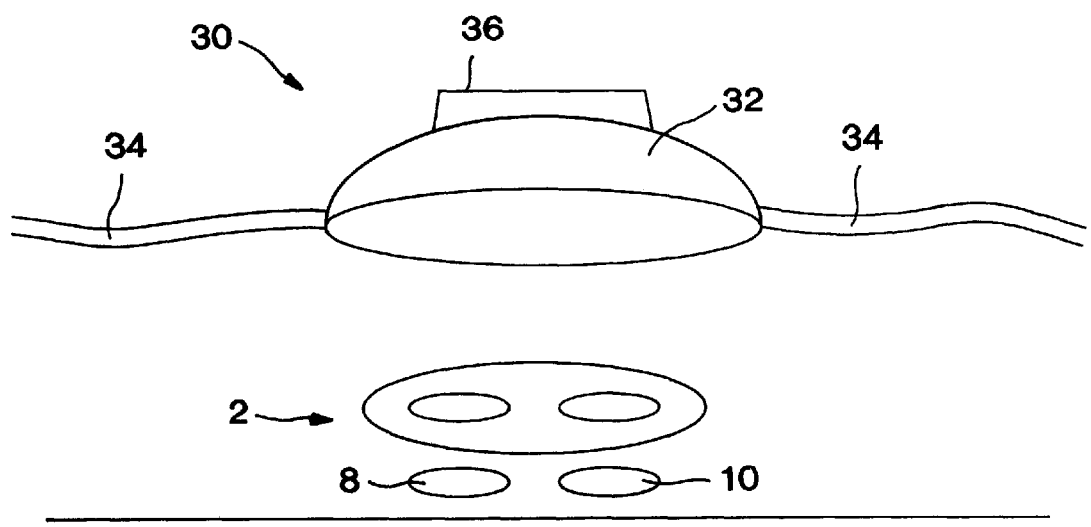
FIG. 2 is a pictorial representation of an iontophoretic sampling device which includes the iontophoretic collection reservoir and electrode assembly of FIGS. 1A and 1B.

Referring now to FIG. 2, the iontophoretic collection reservoir and electrode assembly 2 of FIGS. 1A and 1B is shown in exploded view in combination with a suitable iontophoretic sampling device housing 32. The housing can be a plastic case or other suitable structure which preferably is configured to be worn on a subjects arm in a manner similar to a wrist watch. As can be seen, conductive media 8 and 10 (hydrogel pads) are separable from the assembly 2; however, when the assembly 2 and the housing 32 are assembled to provide an operational iontophoretic sampling device 30, the media are in contact with the electrodes to provide a electrical contact therewith.

Figure 7:
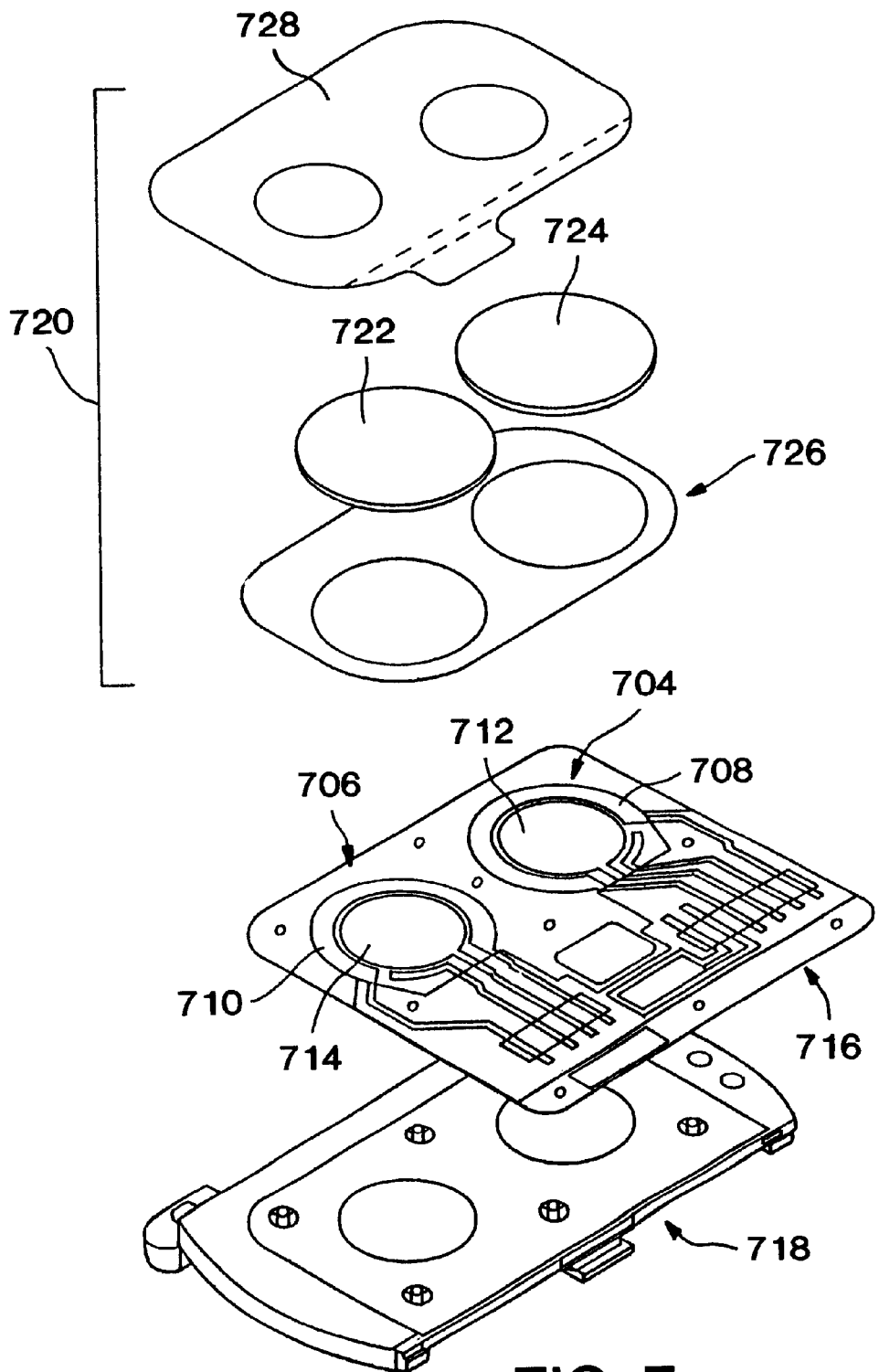
FIG. 7 is an expanded pictorial representation of components comprising one embodiment of an automatic sampling system for use in the practice of the present invention.

Referring now to FIG. 7, an exploded view of the key components from an embodiment of an iontophoretic sampling system is presented. The sampling system components include two biosensor/iontophoretic electrode assemblies, 704 and 706, each of which have an annular iontophoretic electrode, respectively indicated at 708 and 710, which encircles a biosensor 712 and 714. The electrode assemblies 704 and 706 are printed onto a polymeric substrate 716 which is maintained within a sensor tray 718. A collection reservoir assembly 720 is arranged over the electrode assemblies, wherein the collection reservoir assembly comprises two hydrogel inserts 722 and 724 retained by a gel retaining layer 726 and a mask layer 728.

Figure 8:
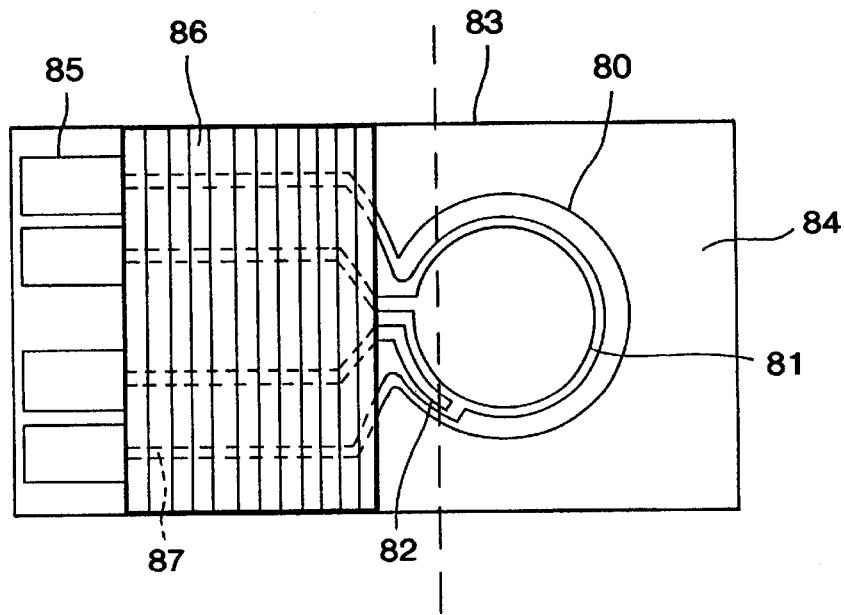
FIG. 8 is a representation of one embodiment of a bimodal electrode design. The figure presents an overhead and schematic view of the electrode assembly 83. In the figure, the bimodal electrode is shown at 80 and can be, for example, a Ag/AgCl iontophoretic/counter electrode. The sensing or working electrode (made from, for example, platinum) is shown at 81. The reference electrode is shown at 82 and can be, for example, a Ag/AgCl electrode. The components are mounted on a suitable nonconductive substrate 84, for example, plastic or ceramic. The conductive leads 87 leading to the connection pad 85 are covered by a second nonconductive piece 86 of similar or different material. In this example of such an electrode the working electrode area is approximately 1.35 $cm^2$. The dashed line in FIG. 8 represents the plane of the cross-sectional schematic view presented in FIG. 9.

In one embodiment, the electrode assemblies can include bimodal electrodes as shown in FIG. 8 and described below.

The components shown in exploded view in FIG. 7 are intended for use in an automatic sampling device which is configured to be worn like an ordinary wristwatch. As described in International Publication No. WO 96/00110, published Jan. 4, 1996, the wristwatch housing (not shown) contains conductive leads which communicate with the iontophoretic electrodes and the biosensor electrodes to control cycling and provide power to the iontophoretic electrodes, and to detect electrochemical signals produced at the biosensor electrode surfaces. The wristwatch housing can further include suitable electronics (e.g., microprocessor, memory, display and other circuit components) and power sources for operating the automatic sampling system.

Modifications and additions to the embodiment of FIG. 7 will be apparent to those skilled in the art in light of the teachings of the present specification.

A power source (e.g., one or more rechargeable or non-rechargeable batteries) can be disposed within the housing 32 or within the straps 34 which hold the device in contact with a skin or mucosal surface of a subject. In use, an electric potential (either direct current or a more complex waveform) is applied between the two iontophoretic electrodes 12 and 14 such that current flows from the first iontophoretic electrode 12, through the first conductive medium 8 into the skin or mucosal surface, and then back out through the second conductive medium 10 to the second iontophoretic electrode 14. The current flow is sufficient to extract substances including an analyte of interest through the skin into one or both of collection reservoirs 4 and 6. The electric potential may be applied using any suitable technique, for example, the applied current density may be in the range of about 0.01 to 0.5 $mA/cm^2$. In a preferred embodiment, the device is used for continual or continuous monitoring, and the polarity of iontophoretic electrodes 12 and 14 is alternated at a rate of about one switch every 10 seconds to about one switch every hour so that each electrode is alternately a cathode or an anode. The housing 32 can further include an optional temperature sensing element (e.g., a thermistor, thermometer, or thermocouple device) which monitors the temperature at the collection reservoirs to enable temperature correction of sensor signals. The housing can also include an optional conductance sensing element (e.g., an integrated pair of electrodes) which monitors conductance at the skin or mucosal surface to enable data screening correction or invalidation of sensor signals.

Figure 9:
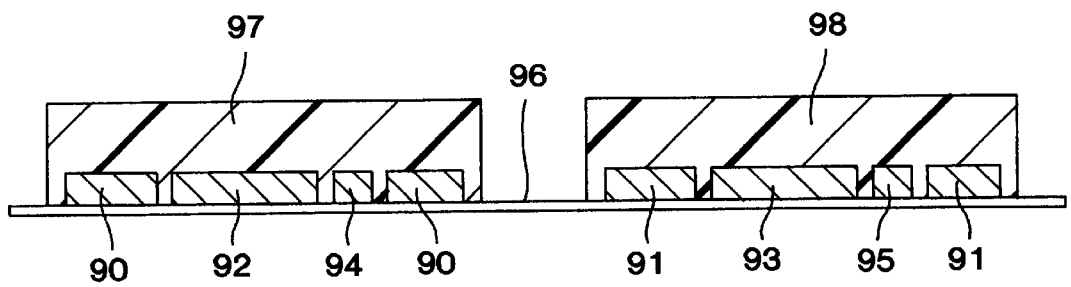
FIG. 9 is a representation of a cross-sectional schematic view of the bimodal electrodes as they may be used in conjunction with a reference electrode and a hydrogel pad. In the figure, the components are as follows: bimodal electrodes 90 and 91; sensing electrodes 92 and 93; reference electrodes 94 and 95; a substrate 96; and hydrogel pads 97 and 98.

In a further aspect, the sampling device can operate in an alternating polarity mode using first and second bimodal electrodes (FIG. 9, 90 and 91) and two collection reservoirs (FIG. 9, 97 and 98). Each bi-modal electrode (FIG. 8, 80; FIG. 9, 90 and 91) serves two functions depending on the phase of the operation: (1) an electro-osmotic electrode (or iontophoretic electrode) used to electrically draw analyte from a source into a collection reservoir comprising water and an electrolyte, and to the area of the electrode subassembly; and (2) as a counter electrode to the first sensing electrode at which the chemical compound is catalytically converted at the face of the sensing electrode to produce an electrical signal.

The reference (FIG. 9, 94 and 95; FIG. 8, 82) and sensing electrodes (FIG. 9, 92 and 93; FIG. 8, 81), as well as, the bimodal electrode (FIG. 9, 90 and 91; FIG. 8, 80) are connected to a standard potentiostat circuit during sensing. In general, practical limitations of the system require that the bimodal electrode will not act as both a counter and iontophoretic electrode simultaneously.

The general operation of an iontophoretic sampling system in this embodiment is the cyclical repetition of two phases: (1) a reverse-iontophoretic phase, followed by a (2) sensing phase. During the reverse iontophoretic phase, the first bimodal electrode (FIG. 9, 90) acts as an iontophoretic cathode and the second bimodal electrode (FIG. 9, 91) acts as an iontophoretic anode to complete the circuit. Analyte is collected in the reservoirs, for example, a hydrogel (FIG. 9, 97 and 98). At the end of the reverse iontophoretic phase, the iontophoretic current is turned off. During the sensing phase, in the case of glucose, a potential is applied between the reference electrode (FIG. 9, 94) and the sensing electrode (FIG. 9, 92). The chemical signal reacts catalytically on the catalytic face of the first sensing electrode (FIG. 9, 92) producing an electrical current, while the first bi-modal electrode (FIG. 9, 90) acts as a counter electrode to complete the electrical circuit.

The electrode described is particularly adapted for use in conjunction with a hydrogel collection reservoir system for monitoring glucose levels in a subject through the reaction of collected glucose with the enzyme glucose oxidase present in the hydrogel matrix.

The bi-modal electrode is preferably comprised of Ag/AgCl. The electrochemical reaction which occurs at the surface of this electrode serves as a facile source or sink for electrical current. This property is especially important for the iontophoresis function of the electrode. Lacking this reaction, the iontophoresis current could cause the hydrolysis of water to occur at the iontophoresis electrodes causing pH changes and possible gas bubble formation. The pH changes to acidic or basic pH could cause skin irritation or burns. The ability of an Ag/AgCl electrode to easily act as a source of sink current is also an advantage for its counter electrode function. For a three electrode electrochemical cell to function properly, the current generation capacity of the counter electrode should not limit the speed of the reaction at the sensing electrode. In the case of a large sensing electrode, the counter electrode should be able to source proportionately larger currents.

The design of the sampling system provides for a larger sensing electrode (see for example, FIG. 8) than previously designed. Consequently, the size of the bimodal electrode should be sufficient so that when acting as a counter electrode with respect to the sensing electrode the counter electrode does not become limiting the rate of catalytic reaction at the sensing electrode catalytic surface.

Two methods exist to ensure that the counter electrode does not limit the current at the sensing electrode: (1) the bi-modal electrode is made much larger than the sensing electrode, or (2) a facile counter reaction is provided.

During the reverse iontophoretic phase, the power source provides a current flow to the first bi-modal electrode to facilitate the extraction of the chemical signal into the reservoir. During the sensing phase, the power source is used to provide voltage to the first sensing electrode to drive the conversion of chemical signal retained in reservoir to electrical signal at the catalytic face of the sensing electrode. The power source also maintains a fixed potential at the electrode where, for example hydrogen peroxide is converted to molecular oxygen, hydrogen ions, and electrons, which is compared with the potential of the reference electrode during the sensing phase. While one sensing electrode is operating in the sensing mode it is electrically connected to the adjacent bimodal electrode which acts as a counter electrode at which electrons generated at the sensing electrode are consumed.

The electrode sub-assembly can be operated by electrically connecting the bimodal electrodes such that each electrode is capable of functioning as both an iontophoretic electrode and counter electrode along with appropriate sensing electrode(s) and reference electrode(s), to create standard potentiostat circuitry.

A potentiostat is an electrical circuit used in electrochemical measurements in three electrode electrochemical cells. A potential is applied between the reference electrode and the sensing electrode. The current generated at the sensing electrode flows through circuitry to the counter electrode (i.e., no current flows through the reference electrode to alter its equilibrium potential). Two independent potentiostat circuits can be used to operate the two biosensors. For the purpose of the present sampling system, the electrical current measured at the sensing electrode subassembly is the current that is correlated with an amount of chemical signal.

With regard to continual operation for extended periods of time, Ag/AgCl electrodes are provided herein which are capable of repeatedly forming a reversible couple which operates without unwanted electrochemical side reactions (which could give rise to changes in pH, and liberation of hydrogen and oxygen due to water hydrolysis). The Ag/AgCl electrodes of the present sampling system are thus formulated to withstand repeated cycles of current passage in the range of about 0.01 to 1.0 mA per $cm^2$ of electrode area. With regard to high electrochemical purity, the Ag/AgCl components are dispersed within a suitable polymer binder to provide an electrode composition which is not susceptible to attack (e.g., plasticization) by components in the collection reservoir, e.g., the hydrogel composition. The electrode compositions are also formulated using analytical- or electronic-grade reagents and solvents, and the polymer binder composition is selected to be free of electrochemically active contaminants which could diffuse to the biosensor to produce a background current.

Since the Ag/AgCl iontophoretic electrodes must be capable of continual cycling over extended periods of time, the absolute amounts of Ag and AgCl available in the electrodes, and the overall Ag/AgCl availability ratio, can be adjusted to provide for the passage of high amounts of charge. Although not limiting in the sampling system described herein, the Ag/AgCl ratio can approach unity. In order to operate within the preferred system which uses a biosensor having a geometric area of 0.1 to 3 $cm^2$, the iontophoretic electrodes are configured to provide an approximate electrode area of 0.3 to 1.0 $cm^2$, preferably about 0.85 2 $cm^2$. These electrodes provide for reproducible, repeated cycles of charge passage at current densities ranging from about 0.01 to 1.0 $mA/cm^2$ of electrode area. More particularly, electrodes constructed according to the above formulation parameters, and having an approximate electrode area of 0.85 $cm^2$, are capable of a reproducible total charge passage (in both anodic and cathodic directions) of 270 mC, at a current of about 0.3 mA (current density of 0.35 $mA/cm^2$) for 48 cycles in a 24 hour period.

Once formulated, the Ag/AgCl electrode composition is affixed to a suitable rigid or flexible nonconductive surface as described above with respect to the biosensor electrode composition. A silver (Ag) underlayer is first applied to the surface in order to provide uniform conduction. The Ag/AgCl electrode composition is then applied over the Ag underlayer in any suitable pattern or geometry using various thin film techniques, such as sputtering, evaporation, vapor phase deposition, or the like, or using various thick film techniques, such as film laminating, electroplating, or the like. Alternatively, the Ag/AgCl composition can be applied using screen printing, pad printing, inkjet methods, transfer roll printing, or similar techniques. Preferably, both the Ag underlayer and the Ag/AgCl electrode are applied using a low temperature screen print onto a polymeric substrate. This low temperature screen print can be carried out at about 125 to 160° C., and the screening can be carried out using a suitable mesh, ranging from about 100–400 mesh.

After a suitable iontophoretic extraction period, one or both of the sensor electrode sets can be activated in order to detect extracted substances including the analyte of interest. Operation of the iontophoretic sampling device 30 can be controlled by a controller 36 (e.g., a microprocessor), which interfaces with the iontophoretic electrodes, the sensor electrodes, the power supply, the optional temperature and/ or conductance sensing elements, a display and other electronics. For example, the controller 36 can include a programmable a controlled circuit source/sink drive for driving the iontophoretic electrodes. Power and reference voltage are provided to the sensor electrodes, and signal amplifiers can be used to process the signal from the working electrode or electrodes. In general, the controller discontinues the iontophoretic current drive during sensing periods. A sensor confidence loop can be provided for continually monitoring the sampling system to insure proper operations.

User control can be carried out using push buttons located on the housing 32, and an optional liquid crystal display (LCD) can provide visual prompts, readouts and visual alarm indications. The microprocessor generally uses a series of program sequences to control the operations of the sampling device, which program sequences can be stored in the microprocessor's read only memory (ROM). Embedded software (firmware) controls activation of measurement and display operations, calibration of analyte readings, setting and display of high and low analyte value alarms, display and setting of time and date functions, alarm time, and display of stored readings. Sensor signals obtained from the sensor electrodes can be processed before storage and display by one or more signal processing functions or algorithms which are stored in the embedded software. The microprocessor can also include an electronically erasable, programmable, read only memory (EEPROM) for storing calibration parameters, user settings and all downloadable sequences. A serial communications port allows the device to communicate with associated electronics, for example, wherein the device is used in a feedback control application to control a pump for delivery of a medicament.

Converting to an Analyte-Specific Value.

In one embodiment, one or more additional "active" collection reservoirs (e.g., each containing the GOx enzyme) can be used to obtain measurements, including raw signal. In one embodiment, two active collection reservoirs are used, and an average is taken between signals from the reservoirs for each measurement time point. Obtaining multiple signals, and then averaging reads from each signals, allows for signal smoothing of unusual data points from a sensor that otherwise may not have been detected by data screening techniques. Furthermore, skin site variability can be detected, and "lag" and/or "lead" differences in blood glucose changes relative to extracted glucose changes can be mitigated. In another embodiment, a second collection reservoir can be provided which serves as a blank (e.g., does not contain the GOx enzyme). This second reservoir can serve as an internal reference (blank) for the sensing device, where a biosensor is used to measure the "blank" signal from the reference reservoir which signal is then used in a blank subtraction step as described below.

A generalized method for continual monitoring of a physiological analyte is disclosed in International Publication No. WO 97/24059, published Jul. 10, 1997, which publication is incorporated herein by reference.

The raw signal is then converted into an analyte-specific value using a calibration step which correlates the signal obtained from the sensing device with the concentration of the analyte present in the biological system. A wide variety of calibration techniques can be used to interpret such signals. These calibration techniques apply mathematical, statistical and/or pattern recognition techniques to the problem of signal processing in chemical analyses, for example, using neural networks, genetic algorithm signal processing, linear regression, multiple-linear regression, or principal components analysis of statistical (test) measurements.

One method of calibration involves estimation techniques. To calibrate an instrument using estimation techniques, it is necessary to have a set of exemplary measurements with known concentrations referred to as the calibration set (e.g., reference set). This set consists of m samples, each with n instrument variables contained in an m by n matrix (X), and an m by 1 vector (y), containing the concentrations. If a priori information indicates the relationship between the measurement and concentration is linear, the calibration will attempt to determine an n by 1 transformation or mapping (b), such that $$y = Xb$$

is an optimal estimate of y according to a predefined criteria. Numerous suitable estimation techniques useful in the practice of the invention are known in the art. These techniques can be used to provide correlation factors (e.g., constants), which correlation factors are then used in a mathematical transformation to obtain a measurement value indicative of the concentration of analyte present in the biological system at the times of measurement.

In one particular embodiment, the calibration step can be carried out using artificial neural networks or genetic algorithms. The structure of a particular neural network algorithm used in the practice of the invention can vary widely; however, the network should contain an input layer, one or more hidden layers, and one output layer. Such networks can be trained on a test data set, and then applied to a population. There are an infinite number of suitable network types, transfer functions, training criteria, testing and application methods which will occur to the ordinarily skilled artisan upon reading the instant specification.

In particular embodiments of the present invention, the detected current can be correlated with the subject's blood glucose concentration (typically using statistical algorithms associated with a microprocessor) so that the system controller may display the subject's actual blood glucose concentration as measured by the sampling system. For example, the system can be calibrated to the subject's actual blood glucose concentration by sampling the subject's blood during a standard glucose tolerance test, and analyzing the blood glucose using both a standard blood glucose monitor and the sampling system of the present invention. In addition or alternately, the sampling system can be calibrated at a calibration time point where the signal obtained from the sampling system at that time point is correlated to blood glucose concentration at that time point as determined by direct blood testing (for example, glucose concentration can be determined using a HemoCue® clinical analyzer (HemoCue AB, Sweden)). In this manner, measurements obtained by the sampling system can be correlated to actual values using known statistical techniques. Such statistical techniques can be formulated as algorithm(s) and incorporated in a microprocessor associated with the sampling system.

In the context of the iontophoretic glucose sampling device described hereinabove, a preferred neural network algorithm could use, for example, the following inputs to provide a blood glucose measurement: time; signal from the active reservoir/signal from the blank reservoir; signal from two active reservoirs (averaged or cumulative); calibration time; skin temperature; voltage; skin conductivity; and, when operating in the training mode, measured glucose.

For example, perspiration contains glucose, and perspiration occurring rapidly and in sufficient quantities may affect the detected signal either before or during biosensor measurement. Accordingly, a sensor can be used to monitor perspiration levels for a given measurement cycle at time points before, during, and/or after iontophoresis, and before, during, and/or after glucose sensing. Although a number of different mechanisms can be used, skin conductance can be readily measured with a device contacted with the skin. Skin conductivity is related to perspiration.

In a similar manner, a sensor can be used to measure skin temperature for a given measurement cycle at time points before, during, and/or after iontophoresis, and before, during, and/or after glucose sensing.

Further, the sampling system can be pre-programmed to begin execution of its signal measurements (or other functions) at a designated time. One application of this feature is to have the sampling system in contact with a subject and to program the sampling system to begin sequence execution during the night so that it is available for calibration immediately upon waking. One advantage of this feature is that it removes any need to wait for the sampling system to warm-up before calibrating it.

Predicting Future or Past Measurements.

The analyte-specific values obtained using the above techniques are used herein to predict future (e.g., time forecasting) or past (e.g., calibration) target analyte concentrations in the biological system. In one preferred embodiment, a series of analyte values are obtained, and these measurements are then used to predict unmeasured analyte values at different points in time, future or past.

More particularly, the above-described iontophoretic sampling process is carried out in order to obtain three or more measurements of the target analyte. Using these measurements, an additional measurement can be calculated. The additional measurement is preferably calculated using a series function as described in greater detail below.

In the context of blood glucose monitoring, it has been found that the actual (real-time) glucose level in a subject differs from the measured glucose level obtained using a sampling device that extracts glucose from the subject using iontophoresis. The difference is due, in part, to a lag time between extracting the glucose analyte and obtaining a measurement from the extracted glucose. This lag time can vary depending on factors such as the particular subject using the device, the particular area of skin from which glucose is extracted, the type of collection reservoir used, and the amount of current applied. In order to compensate for this inherent lag time, the present invention utilizes data obtained from previous measurements and a mathematical function in order to predict what a future analyte concentration will be. In this case, the predicted future reading can be used as a "real-time value" of the analyte level.

In another embodiment, the methods of the invention can be used to predict past measurements, such as in the context of making a calibration. More particularly, measurements obtained using the above-described transdermal sampling device can be calibrated against one or more reference measurements obtained by conventional (blood extraction) methods. In such calibration processes, actual blood glucose levels are determined using conventional methods (e.g., calorimetric methods, spectrophotometric methods, or the like) to analyze an extracted blood sample. These actual measurements are then compared with corresponding measurements obtained with the transdermal sampling device, and a conversion factor is then determined. In normal operations, the transdermal sampling device is generally first contacted with the biological system (placed on the surface of a subject's skin) upon waking. After the device is put in place, it is preferable to wait a period of time in order allow the device to attain normal operating parameters, after which time the device can be calibrated. However, if a blood sample is extracted at the time when the device is first applied (as would normally be most convenient), there may not be a corresponding glucose reading from the transdermal sampling system which can be compared with the reference value obtained from the extracted blood sample. The present method overcomes this problem by allowing one to perform a conventional blood glucose test (via a blood sample extraction) when the device is first applied, and then calibrate the device at a later time.

A number of mathematical methods for predicting future or past measurements can be used in the practice of the invention. For example, linear or polynomial regression analyses, time series analyses, or neural networks can be used to predict such measurements. However, it is preferred that a novel combination of exponential smoothing and a Taylor series analysis be used herein to predict the future or past measurement. This combination is referred to as a Taylor Series Exponential Smoothing (TSES) function.

The TSES function of the present invention was derived from an exponential smoothing function. The method of exponential smoothing calculates the predicted value of a variable (y) at time (n+1) as a function of that variable at the current time (n), as well as at two previous times (n−1) and (n−2). An exponential smoothing equation that is typically used for evenly spaced time points is shown in Equation (1) below, $$y_{n+1} \beta y_n + \beta(1-\beta)y_{n-1} + \beta(1-\beta)^2 y_{n-2} \tag{1}$$

wherein the variable ($\beta$) is an empirical parameter obtained from experimental data, and typically falls between 0 and 1. Adjustments in the value of variable $\beta$ can be made by regressing experimental results and using Equation (1). An improvement to Equation (1) was then made as follows. Since there is a resemblance between Equation (1) and the following conventional Taylor Series expansion function (referred to as Equation (2)), $$f(x) = f(a) + f'(a)(x-a) + \frac{f''(a)(x-a)^2}{2!} + \ldots + \frac{f^{(n-1)}(a)(x-a)^{(n-1)}}{(n-1)!} \tag{2}$$

the variable ($y_{n-1}$) in Equation (1) was replaced with a variable ($y'_n$), which is the first derivative at $y_n$ with respect to time, and the variable (was replaced by a variable ($y''_n/2$), which is the second derivative at $y_n$ with respect to time. This resulted in Equation (3) below, $$y_{n+1} = \beta y_n + \beta(1-\beta)y'_n + \frac{\beta(1-\beta)^2}{2} y''_n \tag{3}$$

where the derivatives are calculated by Equations (4) and (5) as follows:

$$y'_n = \frac{y_n - y_{n-1}}{\Delta t} \tag{4}$$

$$y''_n = \frac{y_n - 2y_{n-1} + y_{n-2}}{\Delta t} \tag{5}$$

and ($\Delta t$) is the equally spaced time interval.

The analogy between Equation (3) and the Taylor Series expansion function of Equation (2) was further improved by dividing the right hand side of Equation (3) by $\beta$ to give Equation (6), where the definition $\alpha=1-\beta$ was used.

$$y_{n+1} = y_n + \alpha y'_n + \frac{\alpha^2}{2} y''_n \tag{6}$$

Finally, by substituting Equations (4) and (5) into Equation (6), the final expression of the TSES function was obtained as:

$$y_{n+1} = y_n + \alpha(y_n - y_{n-1}) + \frac{\alpha^2}{2}(y_n - 2y_{n-1} + y_{n-2}) \tag{7}$$

The TSES function of Equation (7) is essentially an exponentially smoothed moving average Taylor series expansion using the first two terms of the Taylor series. This function can be used to predict $y_{n+1}$, an unmeasured value of the variable y (e.g., blood glucose concentration) at time n+1. The prediction is based on $y_n$, $y_{n-1}$, and $y_{n-2}$, a series of three measurements for y preferably taken at equally spaced time intervals, $\Delta t$. The series of measurements used in the TSES function can be taken at any selected time intervals, and need not be taken at equally spaced time intervals. The function can, of course, be used with a larger series of measurements by using additional terms of the Taylor series. In the context of blood glucose monitoring with an iontophoretic sampling device, the TSES function allows for the accurate prediction of a future (e.g., a "real-time") glucose concentration. In this regard, during a typical iontophoretic measuring cycle, iontophoretic extraction of the analyte is carried out for a suitable amount of time, for example about 1 to 30 minutes, after which time the extracted analyte is detected for a suitable amount of time, for example about 1–30 minutes. These extraction and detection time periods create an inherent lag period of about 2 to 60 minutes between the time at which the analyte is first extracted, and a raw signal has been generated and correlated with the analyte concentration in the biological system.

This inherent lag period can be overcome as follows. In an exemplary iontophoretic measuring cycle, iontophoresis is carried out for a 5 minute interval to extract the glucose analyte through the skin, followed by a 10 minute interval for electrochemical detection of the glucose by the biosensor to obtain the raw signal. This results in a 15 minute lag period. However, by performing a series of these 15 minute measurement cycles, and then applying the TSES function of Equation (7) to the measurement series, the method of the invention allows for an accurate prediction of a future, unmeasured value for y at time n+1 ($y_{n+1}$), substantially reducing or even eliminating the lag period inherent in such iontophoretic measurement periods (by using this future predicted value as the current, real-time value). In preferred applications of the invention, the data sampling interval (in the above example, 15 minutes) should be smaller than the period over which large changes in the value of y (e.g., blood glucose concentrations) are expected to occur, and the data should be sufficiently smooth so that first and second derivatives can be meaningfully calculated.

Figure 3:
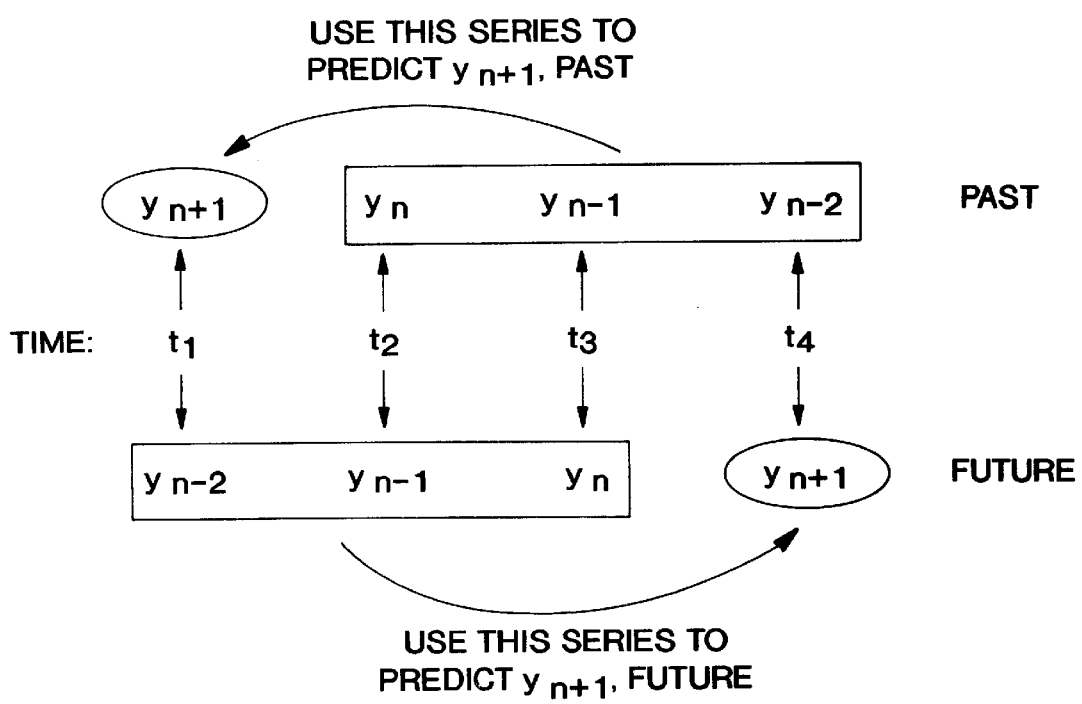
FIG. 3 depicts a time series (times $t_1$, $t_2$, $t_3$, and $t_4$), and two corresponding series of measurements taken in this time series ($y_{n-2} y_{n-1}$ and $y_n$) and ($y_n$, $y_{n-1}$ and $y_{n-2}$) which are respectively used to predict future or past measurements of the variable y at a time n+1 using the method of the invention.

Using similar mathematical techniques, the TSES function of Equation (7) can be used to predict a past unmeasured value based on a series of evenly spaced measurements. In blood glucose monitoring using the above-described iontophoretic sampling device, a blood sample can conveniently be obtained at the same time at which the device is first contacted with the subject's skin, that is, at time zero. After a series of 3 measurements (corresponding to three measurement cycles) have been taken with the iontophoretic device, the TSES function can be solved for a past unmeasured value $y_{n+1}$ (in this case, a time zero measurement) by inserting the measured values for $y_n$, $y_{n-1}$, and $y_{n-2}$ (the series of three measurements) into Equation (7). The actual blood glucose concentration at time zero (obtained from the extracted blood sample) can then be used as a calibration reference value and compared against the predicted time zero measurement. Referring to FIG. 3, time is used in the reverse direction in the TSES function of Equation (7) to predict the past value ($y_{n+1}$). This allows for accurate and reliable calibration of the sampling device using the measured and predicted time zero values.

A number of other physiological variables may be predicted using the above functions. For example, the TSES function of the invention can be used to time forecast those physiological variables that cannot be measured in real-time, or that demonstrate frequent fluctuations in their data. Examples of physiological functions and the variables that characterize them include, but are not limited to, cerebral blood flow (in the treatment of stroke patients) which is related to blood viscosity and the concentrations of plasma proteins and clotting factors in the blood stream (Hachinski, V. and Norris, J. W., "The Acute Stroke," Philadelphia, F A Davis, 1985); pulmonary function (in asthma patients) as measured by lung volumes in the different phases of respiration (Thurlbeck, W. M. (1990) Clin. Chest Med. 11:389); and heart activity (in recurrent cardiac arrest) as measured by electrical activity of the heart (Marriott, H J L, "Practical Electrocardiography", 8th Ed., Baltimore, Williams & Wilkins, 1983). Other examples of physiological variables that can be predicted using the methods of the invention, include renal dialysis, where the blood concentrations of urea and blood gases are followed (Warnock, D. G. (1988) Kidney Int. 34:278); and anesthesia treatment, where various parameters (e.g., heart rate, blood pressure, blood concentration of the anesthesia) are monitored to determine when the anesthesia will stop functioning (Vender, J. S., and Gilbert, H. C., "Monitoring the Anesthetized Patient," in Clinical Anesthesia, 3rd Ed., by Barash et al., Lippincott-Raven Publishers, Philadelphia, 1996).

Controlling a Physiological Effect.

Predicted analyte values obtained with the above techniques can also be used to control an aspect of the biological system. e.g., a physiological effect. In one embodiment, the predicted analyte value is used to determine when, and at what level, a constituent should be added to the biological system in order to control the concentration of the target analyte.

More particularly, in the context of blood glucose monitoring, use of the TSES function of Equation (7) allows for accurate predictions of either real-time or future blood glucose values. This is of particular value in predicting hypoglycemic episodes which can lead to diabetic shock, or even coma. Having a series of measurements obtained from the continual iontophoretic sampling device, and the capability to predict future values using Equation (7), allows a subject to detect blood glucose swings or trends indicative or hypoglycemic or hyperglycemic episodes prior to their reaching a critical level, and to compensate therefor by way of exercise, diet or insulin administration.

A feedback control application of the present invention entails using the TSES function of Equation (7) to predict real-time blood glucose levels, or measurement of future blood glucose levels, and then using these predicted signals to control a pump for insulin delivery to treat hyperglycemia.

EXAMPLES

The following examples are put forth so as to provide those of ordinary skill in the art with a complete disclosure and description of how to make and use the devices, methods, and formulae of the present invention, and are not intended to limit the scope of what the inventor regards as his invention. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Prediction of Measurement Values

Iontophoretic extraction of glucose was carried out using a low-level iontophoretic current to extract glucose through patient's skin and an electrochemical biosensor to detect the extracted glucose. Iontophoresis was carried out for 5 minute intervals and electrochemical detection was carried out for 10 minute intervals to result in 15 minute measurement cycles.

Figure 4:
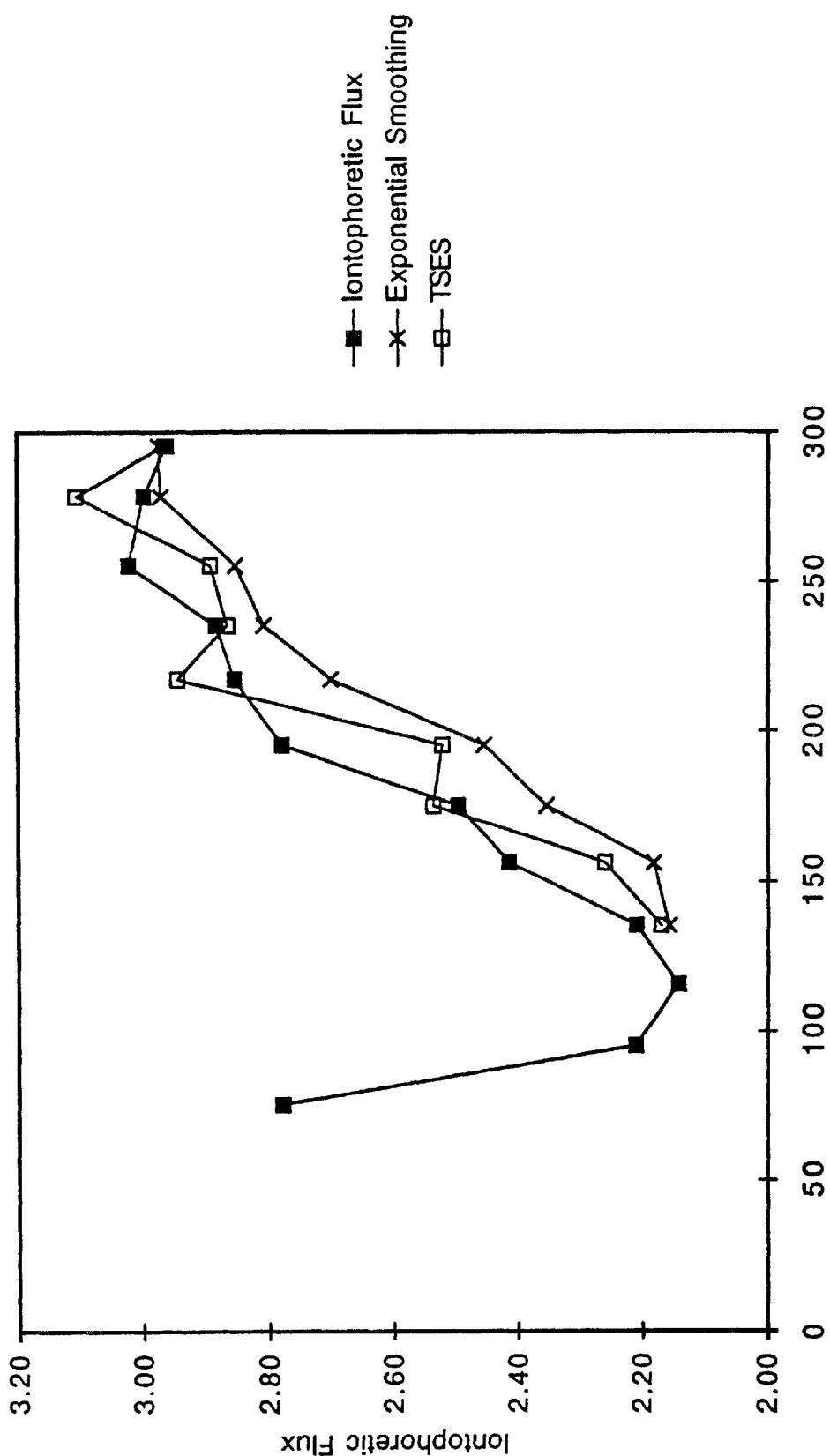
FIGS. 4, 5, and 6 depict experimental iontophoretic flux data compared with predicted values obtained using the method of the invention.
Figure 5:
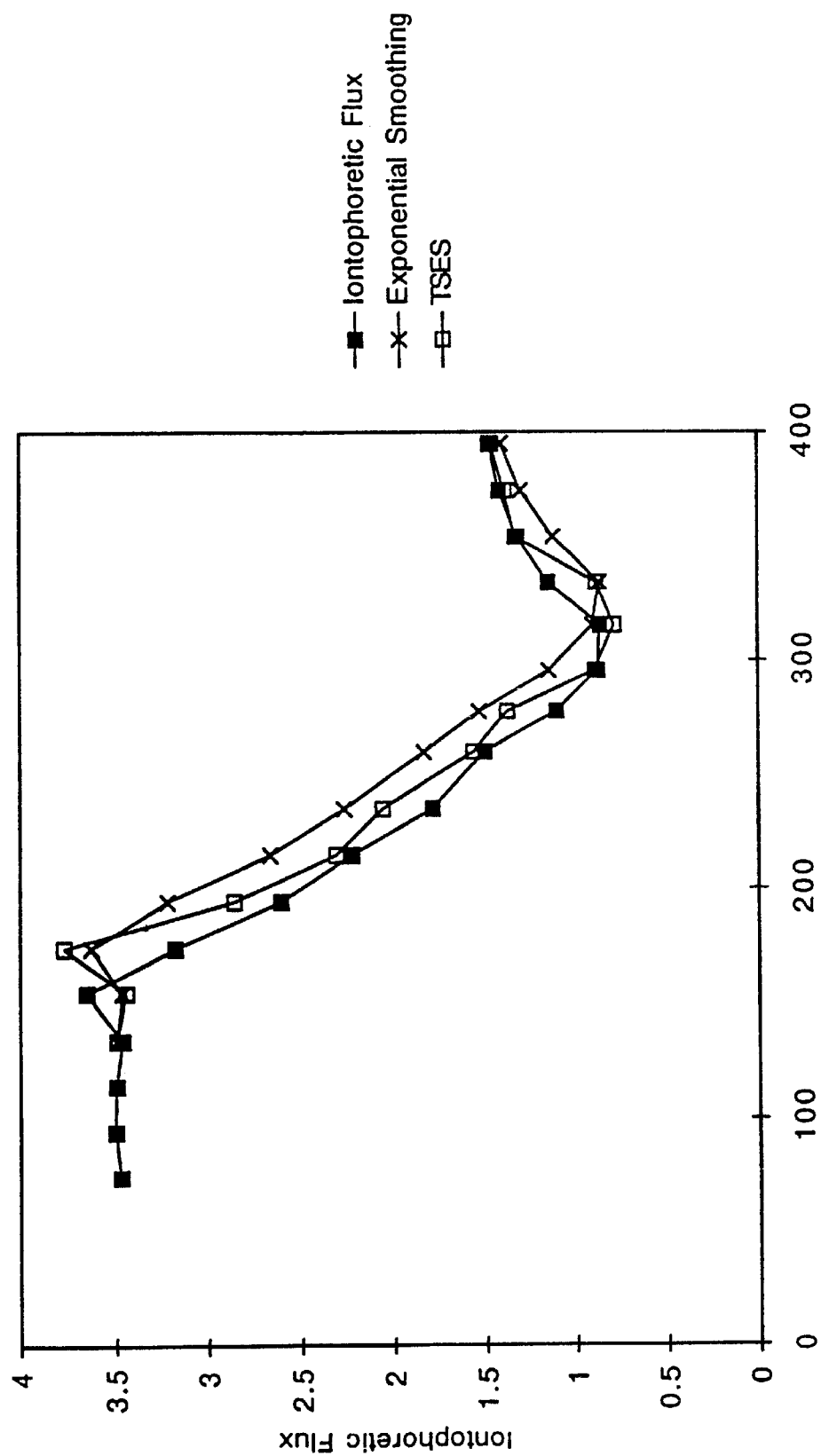
Figure 6:
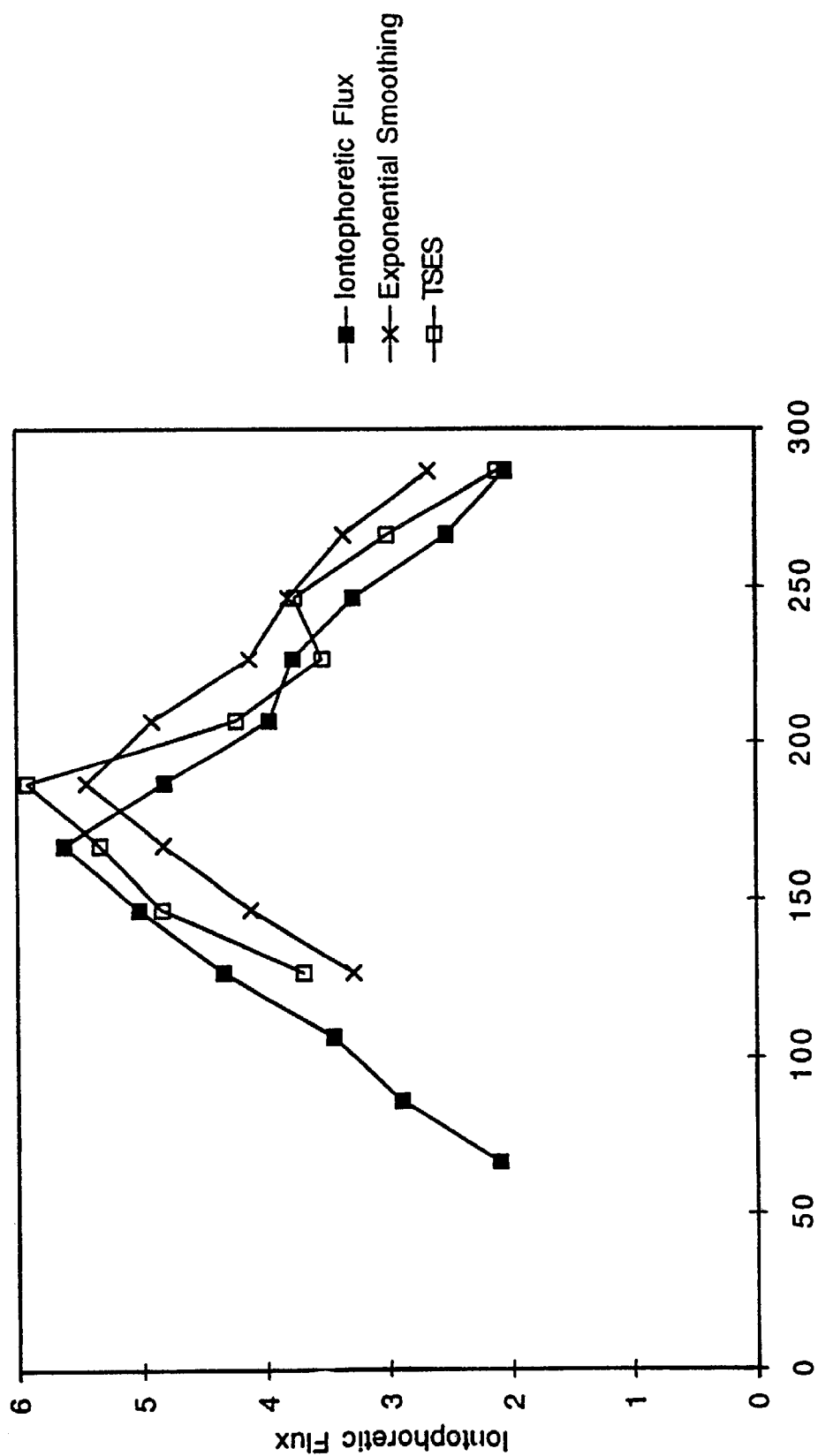

Iontophoretic flux data thus obtained are displayed in FIGS. 4–6. These measured data are represented by the (■) data points. Superimposed in these figures are the predicted iontophoretic flux at time n+1, represented by the (□) data points, wherein the predicted values were obtained using the TSES function of Equation (7). Also shown are predicted values obtained using the exponential smoothing function of Equation (1), represented by the (X) data points. The value of $\alpha$ used in the TSES function prediction was $\alpha=0.5$, and the value $\beta$ that was used in the exponential smoothing function was $\beta=0.8$. The average RMS error between predicted flux data obtained using the TSES function of Equation (7) and the actual flux data was found to be 10.2%, while the average RMS error between the predicted flux data obtained using the smoothing function of Equation (1) and the actual flux data was found to be 12.3%. These results indicate that the TSES function of the present invention provides a twenty-percent improvement in the accuracy of predicted analyte values when compared with conventional exponential smoothing techniques.

What is claimed is:

1. A method for measuring an analyte present in a biological system, said method comprising:
    (a) transdermally extracting the analyte from the biological system using a sampling system that is in operative contact with a skin or mucosal surface of said biological system;
    (b) obtaining a raw signal from the extracted analyte, wherein said raw signal is specifically related to the analyte;
    (c) performing a calibration step which correlates the raw signal obtained in step (b) with a measurement value indicative of the concentration of analyte present in the biological system at the time of extraction;
    (d) repeating steps (a)–(b) to obtain a series of measurement values at selected time intervals, wherein the sampling system is maintained in operative contact with the skin or mucosal surface of said biological system to provide for analyte measurement; and
    (e) predicting a measurement value at a further time interval which occurs either one time interval before or one time interval after the series of measurement values is obtained in step (d).

2. The method of claim 1, wherein the selected time intervals are evenly spaced.

3. The method of claim 1, wherein the series of measurement values obtained in step (d) is comprised of three or more discrete values.

4. The method of claim 3, wherein the further time interval occurs one time interval after the series of measurement values is obtained in step (d).

5. The method of claim 3, wherein the further time interval occurs one time interval before the series of measurement values is obtained in step (d).

6. The method of claim 3, wherein the prediction of step (e) is carried out using said series of three or more measurement values in a series function represented by:

$$y_{n+1} = y_n + \alpha(y_n - y_{n-1}) + \frac{\alpha^2}{2}(y_n - 2y_{n-1} + y_{n-2}) \quad (7)$$

wherein y is the measurement value of the analyte, n is the time interval between measurement values, and $\alpha$ is a real number between 0 and 1.

7. The method of claim 6, wherein the series function is used to predict the value of $y_{n+1}$ and the time interval n+1 occurs one time interval after the series of measurement values is obtained.

8. The method of claim 6, wherein the series function is used to predict the value of $y_{n+1}$ and the time interval n+1 occurs one time interval before the series of measurement values is obtained.

9. The method of claim 8, further comprising the step of taking a reference analyte measurement at the time interval n+1.

10. The method of claim 1, wherein the analyte is extracted from the biological system in step (a) into a collection reservoir to obtain a concentration of the analyte in said reservoir.

11. The method of claim 10, wherein the collection reservoir is in contact with the skin or mucosal surface of the biological system and the analyte is extracted using an iontophoretic current applied to said skin or mucosal surface.

12. The method of claim 11, wherein the collection reservoir contains an enzyme that reacts with the extracted analyte to produce an electrochemically detectable signal.

13. The method of claim 12, wherein the analyte is glucose and the enzyme is glucose oxidase.

14. The method of claim 13, wherein the series of measurement values obtained in step (d) is comprised of three or more discrete blood glucose values.

15. The method of claim 14, wherein the further time interval occurs one time interval after the series of measurement values is obtained in step (d).

16. The method of claim 14, wherein the further time interval occurs one time interval before the series of measurement values is obtained in step (d).

17. The method of claim 14, wherein the prediction of step (e) is carried out using said series of three or more measurement values in a series function represented by:

$$y_{n+1} = y_n + \alpha(y_n - y_{n-1}) + \frac{\alpha^2}{2}(y_n - 2y_{n-1} + y_{n-2}) \quad (7)$$

wherein y is the measurement value of blood glucose, n is the time interval between measurement values, and a is a real number between 0 and 1.

18. The method of claim 17, wherein the series function is used to predict the value of $y_{n+1}$, and the time interval n+1 occurs one time interval after the series of measurement values is obtained.

19. The method of claim 18, wherein the predicted value of $y_{n+1}$ is used to control administration of insulin to the biological system from an associated insulin pump.

20. The method of claim 17, wherein the series function is used to predict the value of $y_{n+1}$ and the time interval n+1 occurs one time interval before the series of measurement values is obtained.

21. The method of claim 20, further comprising the step of taking a reference blood glucose measurement from the biological system at the time interval n+1.

22. The method of claim 21, wherein the reference blood glucose measurement is compared against the predicted value of $y_{n+1}$ and used to calibrate the sampling device.

23. A method for measuring blood glucose in a subject, said method comprising:
   (a) operatively contacting a glucose sensing apparatus with the subject to detect blood glucose;
   (b) obtaining a raw signal from the sensing apparatus, wherein said raw signal is specifically related to the glucose detected by the sensing apparatus;
   (c) performing a calibration step which correlates the raw signal obtained in step (b) with a measurement value indicative of the subject's blood glucose concentration;
   (d) repeating steps (a)–(b) to obtain a series of measurement values at selected time intervals; and
   (e) predicting a measurement value at a further time interval which occurs either one time interval before or one time interval after the series of measurement values is obtained in step (d).

24. The method of claim 23, wherein the sensing means comprises an enzyme that reacts with the glucose to produce an electrochemically detectable signal.

25. The method of claim 24, wherein the enzyme is glucose oxidase.

26. The method of claim 23, wherein the sensing apparatus is a near-IR spectrometer.

27. The method of claim 23, wherein the selected time intervals are evenly spaced.

28. The method of claim 23, wherein the series of measurement values obtained in step (d) is comprised of three or more discrete values.

29. The method of claim 28, wherein the further time interval occurs one time interval after the series of measurement values is obtained in step (d).

30. The method of claim 28, wherein the further time interval occurs one time interval before the series of measurement values is obtained in step (d).

31. The method of claim 28, wherein the prediction of step (e) is carried out using said series of three or more measurement values in a series function represented by:

$$y_{n+1} = y_n + \alpha(y_n - y_{n-1}) + \frac{\alpha^2}{2}(y_n - 2y_{n-1} + y_{n-2}) \quad (7)$$

wherein y is the measurement value of the analyte, n is the time interval between measurement values, and $\alpha$ is a real number between 0 and 1.

32. The method of claim 31, wherein the series function is used to predict the value of $y_{n+1}$ and the time interval n+1 occurs one time interval after the series of measurement values is obtained.

33. The method of claim 31, wherein the series function is used to predict the value of $y_{n+1}$ and the time interval n+1 occurs one time interval before the series of measurement values is obtained.

34. The method of claim 33, further comprising the step of taking a reference analyte measurement at the time interval n+1.

35. A monitoring system for measuring an analyte present in a biological system, said system comprising, in operative combination:

(a) sampling means for extracting the analyte from the biological system, wherein said sampling means is adapted for extracting the analyte across a skin or mucosal surface of said biological system;

(b) sensing means in operative contact with the analyte extracted by the sampling means, wherein said sensing means obtains a raw signal from the extracted analyte and said raw signal is specifically related to the analyte; and (c) microprocessor means in operative communication with the sampling means and the sensing means, wherein said microprocessor means (i) is used to control the sampling means and the sensing means to obtain a series of raw signals at selected time intervals during a measurement period, (ii) correlate the raw signals with measurement values indicative of the concentration of analyte present in the biological system, and (iii) predict a measurement value at a further time interval which occurs either one time interval before or one time interval after the series of measurement values is obtained.

36. The monitoring system of claim 35, wherein the sensing means comprises a near-IR spectrometer.

37. The monitoring system of claim 35, wherein the measurement values comprise a series of measurement values comprising three or more discrete values.

38. The monitoring system of claim 37, wherein the further time interval occurs one time interval after the series of measurement values.

39. The monitoring system of claim 37, wherein the further time interval occurs one time interval before the series of measurement values.

40. The monitoring system of claim 37, wherein the prediction of (c)(iii) is carried out using said series of three or more measurement values in a series function represented by:

$$y_{n+1} = y_n + \alpha(y_n - y_{n-1}) + \frac{\alpha^2}{2}(y_n - 2y_{n-1} + y_{n-2}) \tag{7}$$

wherein y is the measurement value of the analyte, n is the time interval between measurement values, and $\alpha$ is a real number between 0 and 1.

41. The monitoring system of claim 40, wherein the series function is used to predict the value of $y_{n+1}$, and the time interval n+1 occurs one time interval after the series of measurement values is obtained.

42. The monitoring system of claim 40, wherein the series function is used to predict the value of $y_{n+1}$ and the time interval n+1 occurs one time interval before the series of measurement values is obtained.

43. The monitoring system of claim 35, wherein the sampling means includes one or more collection reservoirs for containing the extracted analyte.

44. The monitoring system of claim 35, wherein the sampling means uses an iontophoretic current to extract the analyte from the biological system.

45. The monitoring system of claim 44, wherein the collection reservoir contains an enzyme that reacts with the extracted analyte to produce an electrochemically detectable signal.

46. The monitoring system of claim 45, wherein the analyte is glucose and the enzyme is glucose oxidase.

* * * * *